United States Patent
Steensels et al.

(10) Patent No.: US 12,180,460 B2
(45) Date of Patent: Dec. 31, 2024

(54) LONG-LIVING, THERMOTOLERANT YEAST AND USE THEREOF IN PRODUCING A FERMENTED BEVERAGE

(71) Applicant: DUVEL MOORTGAT NV, Puurs-Sint-Amands (BE)

(72) Inventors: Jan Steensels, Lommel (BE); Kevin Verstrepen, Leuven (BE); Ruben Wauters, Tremelo (BE); Scott Britton, Puurs-Sint-Amands (BE); Michel Moortgat, Puurs-Sint-Amands (BE); Hedwig Neven, Puurs-Sint-Amands (BE)

(73) Assignee: DUVEL MOORTGAT NV, Puurs-Sint-Amands (BE)

( * ) Notice: Subject to any disclaimer, the term of this patent is extended or adjusted under 35 U.S.C. 154(b) by 119 days.

(21) Appl. No.: 17/997,959

(22) PCT Filed: May 7, 2021

(86) PCT No.: PCT/IB2021/053890
§ 371 (c)(1),
(2) Date: Nov. 4, 2022

(87) PCT Pub. No.: WO2021/224875
PCT Pub. Date: Nov. 11, 2021

(65) Prior Publication Data
US 2023/0174923 A1 Jun. 8, 2023

(30) Foreign Application Priority Data
May 7, 2020 (BE) .................................. 2020/5309

(51) Int. Cl.
C12N 1/18 (2006.01)
C12C 12/00 (2006.01)
C12R 1/865 (2006.01)

(52) U.S. Cl.
CPC ............ *C12N 1/185* (2021.05); *C12C 12/006* (2013.01); *C12R 2001/865* (2021.05)

(58) Field of Classification Search
CPC .......... C12N 1/185; C12N 15/04; C12N 1/18; C12C 12/006; C12R 2001/865; A23L 2/382
See application file for complete search history.

(56) References Cited

FOREIGN PATENT DOCUMENTS

WO 2021/224875 A1 11/2021

OTHER PUBLICATIONS

Sato M, Kishimoto M, Watari J, Takashio M. Breeding of brewer's yeast by hybridization between a top-fermenting yeast *Saccharomyces cerevisiae* and a cryophilic yeast *Saccharomyces bayanus*. J Biosci Bioeng. 2002;93(5):509-11. doi: 10.1016/s1389-1723(02)80101-3. PMID: 16233241. (Year: 2002).*
Wikipedia—Gravity of alcoholic beverage definition, 6 page of PDF, retrieved from Wikipedia.com on Aug. 8, 2024. (Year: 2024).*
Written Opinion and International Search Report for PCT Application No. PCT/IB2021/053890 mailed Aug. 25, 2021.
Meersman E. et al., "Breeding Strategy To Generate Robust Yeast Starter Cultures for Cocoa Pulp Fermentations", Applied and Environmental Microbiology, vol. 81, No. 18, Sep. 15, 2015 (Sep. 15, 2015), p. 6166-6176.
Krogerus K. et al., "Novel brewing yeast hybrids: creation and application", Nov. 24, 2016 (Nov. 24, 2016), vol. 101, No. 1, p. 65-78.
Steensels J. et al., "Large-Scale Selection and Breeding To Generate Industrial Yeasts with Superior Aroma Production", Applied and Environmental Microbiology, vol. 80, No. 22, Nov. 15, 2014 (Nov. 15, 2014), p. 6965-6975.
Steensels J. et al., "Improving industrial yeast strains: exploiting natural and artificial diversity", FEMS Microbiology Reviews, vol. 38, No. 5, Sep. 1, 2014 (Sep. 1, 2014), p. 947-995.
Bonciani T. et al., "Improved wine yeasts by direct mating and selection under stressful fermentative conditions", Nov. 25, 2015 (Nov. 25, 2015), vol. 242, No. 6, p. 899-910.
Zunar B. et al., "Novel approach in developing *Saccharomyces cerevisiae* hybrid bioethanol producers by mating of natural isolates having desirable traits", Journal of Biotechnology, vol. 280, Aug. 1, 2018 (Aug. 1, 2018), page S89.
Gallone B. et al., "Domestication and Divergence of *Saccharomyces cerevisiae* Beer Yeasts", Cell, vol. 166, No. 6, Sep. 8, 2016 (Sep. 8, 2016), p. 1397-1410.
Gallone B. et al., "Interspecific hybridization facilitates niche adaptation in beer yeast", Nature Ecology & Evolution, vol. 3, No. 11, Oct. 21, 2019 (Oct. 21, 2019), p. 1562-1575.
Steensels J. et al., "Interspecific hybridization as a driver of fungal evolution and adaptation", Mar. 25, 2021 (Mar. 25, 2021), vol. 19, No. 8, p. 485-500.

* cited by examiner

*Primary Examiner* — Kade Ariani
(74) *Attorney, Agent, or Firm* — Vorys, Sater, Seymour and Pease, LLP

(57) ABSTRACT

The present invention relates to a yeast strain used in the production of a fermented beverage, wherein the yeast strain is a hybrid obtained by a mass-mating hybridisation process between haploid spores selected from *Saccharomyces cerevisiae* strain Y927, strain Y115, strain WI011, strain WI017 and strain WI018, or wherein the yeast strain is an inbred strain of said hybrid. The present invention further relates to a yeast slurry, a method for brewing a fermented beverage, and a malt or tea-based beverage obtained on the basis of a fermentation process.

12 Claims, 6 Drawing Sheets

FIGURES

LONG-LIVING, THERMOTOLERANT YEAST AND USE THEREOF IN PRODUCING A FERMENTED BEVERAGE

TECHNICAL FIELD

The invention relates to a yeast strain used in the production of a fermented beverage, wherein the yeast strain is a hybrid obtained by a hybridisation process between haploid spores of parental yeast strains, or wherein the yeast strain is an inbred strain of said hybrid. The invention further relates to a yeast slurry, a method for brewing a fermented beverage, and a beverage obtained on the basis of a fermentation process.

PRIOR ART

Once a fermented beverage, such as beer, leaves the brewery, it undergoes a series of chemical, physical, and sensory transformations that lead to changes in taste and overall quality. Controlling and slowing down these changes, which are called 'staling' in English, is the subject of much research in the fermented beverage landscape, including the beer landscape. One of the symptoms of 'staling' is a loss of quality due to an increase in bad-tasting components in the beverage. Slowing down the 'aging' of these beverages namely increases the shelf life of these products, and as a result has both a commercial advantage and a positive effect on the durability of the product.

The process for brewing beer can be roughly summarised as follows: a first step is malting, where barley is moistened, germinated and then dried. The result of this step is called malt. During the next step, the mashing step, the malt is then ground, also called milling, and mixed with warm water to expose the malt to enzymatic activity. These enzymes convert starch into simple sugars and proteins into peptides and amino acids. The dissolved product from the mashing step is called 'wort' and is separated from the non-soluble residues (mostly chaff of the barley), referred to as draff, by filtration. The wort thus obtained is then boiled with the addition of hops. Boiling deactivates the enzymes, sterilises the wort, extracts desired hop components and coagulates some proteins. Hops are added to the boiling mixture to impart bitterness and aroma. After cooling the wort, yeast is added to convert the sugar into alcohol and carbon dioxide during the fermentation. After fermentation, most of the yeast is harvested, leaving the so-called 'green beer'. This green beer with the remaining yeast cells is stored at a low temperature for several weeks, a process called 'lagering'. Towards the end of the lagering there is a sediment in the tank consisting of yeast cells and precipitated protein and polyphenols. This mixture is filtered and finally the beer is transferred to the bottling or keg filling machine and stored in bottles and kegs, respectively.

A promising strategy to counteract the aging or staling of beer is the use of so-called 'bottle conditioning', wherein the yeast cells are inoculated into the beer before the beer is packaged. The exact mechanism is unknown, but it is expected that the reducing metabolism of live yeast cells on the one hand removes the remaining oxygen in the bottle, preventing oxidative degradation reactions, and on the other hand ensures chemical conversion of 'staling' components, such as converting 'staling' aldehydes to their corresponding and less taste negative alcohols.

One of these aldehydes is furfural, a component that can be reduced by yeasts to furfuryl alcohol. Furfural is often used as an aldehyde indicator and to predict and/or determine the aging and quality of the beverage. The longer the yeast strain remains alive in the fermented beverage, the longer it can counter the build-up of furfural and other aldehydes, the longer the taste and quality of the beverage will remain good, and the longer the shelf life will be.

However, environmental conditions in a beverage bottle, such as a high temperature during transport and a high alcohol percentage, are extremely stressful for the yeast cells, leading to cell death and thus to gradual reduction of the anti-staling properties.

It is an object of the invention to provide yeast strains that are tolerant to at least some of these environmental conditions so that they can reduce the 'staling' of the beer over a longer period of time and in a wider range of environmental conditions, and to provide a method for brewing alcoholic fermented beverage through these yeast cells.

SUMMARY OF THE INVENTION

The invention relates to a yeast strain used in the production of a fermented beverage according to claim 1. More specifically, the invention relates to a hybrid obtained by a mass-mating hybridisation process between haploid spores selected from *Saccharomyces cerevisiae* strain Y927, strain Y115, strain WI011, strain WI017 and strain WI018, or an inbred strain of this hybrid. This yeast strain is thermotolerant and long-living. In a second aspect, the invention relates to a yeast slurry according to claim 8. Preferred embodiments are set out in claims 2-7 and in claims 9-12, respectively.

In a further aspect, the invention relates to a method for brewing a fermented beverage using a yeast strain or yeast slurry obtained by a mass-mating hybridisation process between haploid spores selected from *saccharomyces cerevisiae* strain Y927, strain Y115, strain WI011, strain WI017 and strain WI018, or wherein the yeast strain is an inbred strain of said hybrid is added to a beverage. In addition, the invention also relates to a malt or tea-based beverage obtained on the basis of a fermentation process using a yeast strain or yeast slurry obtained by a mass-mating hybridisation process between haploid spores selected from *Saccharomyces cerevisiae* strain Y927, strain Y115, strain WI011, strain WI017 and strain WI018, or wherein the yeast strain is an inbred strain of said hybrid is added to a beverage.

The yeast strain, the yeast slurry or its use in the method or in the malt or tea-based beverage, improves the quality and extends the shelf life of a fermented beverage due to its anti-staling properties. Longevity, as well as tolerance of the yeast strain to more extreme environmental conditions, results in a commercial advantage, given the market for fermented beverages is global, and given the way these beverages are transported around the world in a variety of environmental conditions.

DEPOSIT INFORMATION

Figure 1:
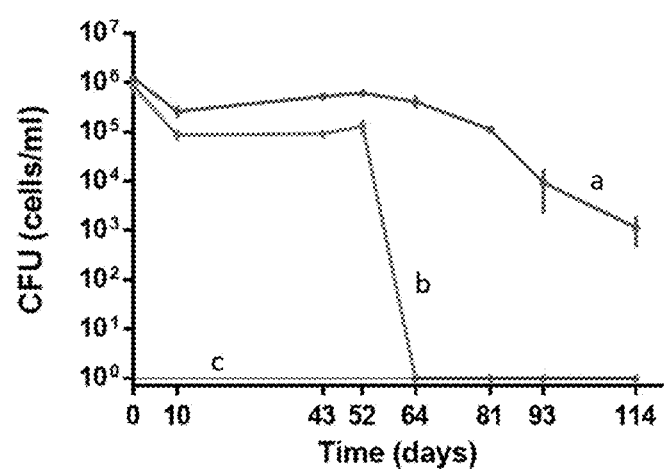
FIG. 1 schematically shows the number of live yeast cells of two yeast strains per ml in beer over time.

Strains of the present invention (i.e., BCCM 58105 and 58106, which are hybrids obtained by a mass-mating hybridisation process between haploid spores selected from *Saccharomyces cerevisiae* strain Y927, strain Y115, strain WI011, strain WI017 and strain WI018) have been deposited on Mar. 17, 2021 at the Belgian Coordinated Collection of Microorganisms (BCCM)—Universite catholique de Louvain—Mycotheque de l'Université catholique de Louvain (MUCL), Croix du Sud 2, box L7. 05.06, 1348 Louvain-la-neuve, Belgium under the terms of the Budapest Treaty, with Deposit ID numbers: 58105 and 58106.

DETAILED DESCRIPTION OF THE INVENTION

The invention relates to a yeast strain used in the production of a fermented beverage, a yeast slurry, a method for brewing a fermented beverage and a malt or tea-based beverage obtained on the basis of a fermentation process.

Unless otherwise defined, all terms used in the description of the invention, including technical and scientific terms, have the meaning as commonly understood by a person skilled in the art to which the invention pertains. For a better understanding of the description of the invention, the following terms are explained explicitly.

In this document, 'a' and 'the' refer to both the singular and the plural, unless the context presupposes otherwise. For example, 'a segment' means one or more segments.

When the term 'around' or 'about' is used in this document with a measurable quantity, a parameter, a duration or moment, and the like, then variations are meant of approx. 20% or less, preferably approx. 10% or less, more preferably approx. 5% or less, even more preferably approx. 1% or less, and even more preferably approx. 0.1% or less than and of the quoted value, insofar as such variations are applicable in the described invention. However, it must be understood that the value of a quantity used where the term 'about' or 'around' is used, is itself specifically disclosed.

The terms 'comprise', 'comprising', 'consist of', 'consisting of', 'provided with', 'have', 'having', 'include', 'including', 'contain', 'containing' are synonyms and are inclusive or open terms that indicate the presence of what follows, and which do not exclude or prevent the presence of other components, characteristics, elements, members, steps, as known from or disclosed in the prior art.

Quoting numerical intervals by endpoints comprises all integers, fractions and/or real numbers between the endpoints, these endpoints included.

The term 'fermentation', in the present context refers to the enzymatic conversion of sugars in a liquid or beverage by the action of one or more yeasts. In the context of beer, the term 'fermentation' refers to the conversion of sugars into wort, by enzymes in the brewing yeast, into alcohol (e.g. ethanol) and carbon dioxide with the formation of other fermentation by-products including organic acids and esters.

The term 'wort' refers to a sugar-rich, unfermented liquid produced from malt, wheat or other grain during brewing, as in the brewing of beer or other distilled malt liquors or beverages.

By the term 'yeast' is meant a single-celled eukaryote, belonging to the fungi. The main yeasts used in a brewery, also called 'barms' or 'brewer's yeasts', are *Saccharomyces eubayanus* (also called *Saccharomyces carlsbergensis*) and *Saccharomyces cerevisiae*. They both belong to the Saccharomycesceae family and the Saccharomyceseae subfamily. This subfamily is characterised by the occurrence of spores in an ascus and by budding propagation. The genus *Saccharomyces*, abbreviated to S., is mainly characterised by the occurrence of an alcoholic fermentation. A distinction between the two yeasts is based on whether the yeast rises or settles during fermentation. Yeast that settles is called 'low' yeast, yeast that rises 'high' yeast. *S. carlsbergensis* is a low yeast, *S. cerevisiae* a high one.

'Refermentation', also called 'secondary fermentation', 'after-fermentation' or 'post-fermentation', means that a second or sometimes third fermentation of the wort continues in a, usually new fermenter, after a first or primary fermentation step. This will remove some of the yeast from the beverage. During this second fermentation, most of the remaining yeast will settle to the bottom of the fermentation vessel, creating a less cloudy product. This also gives the opportunity to allow the fermenting beverage to mature. Refermentation by adding *Saccharomyces* or another yeast will give the beer its specific taste and colour. The reducing character of the yeast will also prevent oxidation processes.

By 'hybrid' in present context is meant the result of sexual reproduction of two different parental yeasts. The 'hybridisation process' is the crossing of different yeasts to form hybrids and involves three main steps. Firstly, spore formation is induced (sporulation), after which these spores are isolated and finally the actual hybridisation follows, which depends on the fusion of these spores or of haploid cells that are produced from the spores by budding.

Two types of hybridisation can occur, namely outbreeding and inbreeding. 'Outbreeding' is when two parental strains are selected on the basis of one or more interesting features (e.g., thermotolerance and/or survival) and sporulate them. This means that the parental yeast cells (with 'double' DNA content or 'diploids') are activated to form cells with only half the original DNA content ('haploids'). Haploid spores of those different parental cells, with an opposite mating type (a or α), are brought together and fuse into new diploids. These yeast strains then have DNA from both parents, resulting in cells with different properties, some of which are better than the original parents: hybrids.

'Inbreeding' is done in the same way, but only one parental yeast strain is assumed. Since haploid formation causes rearrangements in the DNA, the spores from a single parent will all be different. Mating these spores will therefore also yield other yeast strains than (and possibly better than) their parent strain. These yeast strains are referred to in this context as 'inbred strains'.

A yeast strain has a unique genetic fingerprint or unique genetic profile. Based on this profile, and the profiles of the two parent strains, it can be determined whether the new yeast strain is the result of inbreeding or outbreeding. Alternatively, DNA sequencing can also be used to determine which type of hybridisation has occurred. In addition, other techniques can also be used, as known by a person skilled in the art.

'Long-living' is defined in the context of the present invention as being able to perform metabolic and/or enzymatic activity, at least for 100 days. An easily measurable and visual example of this is growth and/or cell division, but this metabolic and/or enzymatic activity is not limited to growth and/or cell division. 'Longevity', ' . . . that can survive for a long time', ' . . . that survives for a long time', and similar terms as will be apparent to one of skill in the art are included in this definition in the present context.

A 'malt-based beverage' is a fermented beverage in which the primary ingredient is the grain, or seed, of the barley plant, which has been allowed to germinate in a traditional manner, called 'malting', before being processed. The most famous malt-based beverage is beer. In addition, the term malt-based beverage is applied to many other flavoured beverages prepared from malted grains and to which natural or artificial flavours (and sometimes colours) have been added to make them taste and resemble wines, fruits, colas, natural ciders or other beverages.

A 'tea-based beverage' is a beverage whose base is tea. Tea is a hot beverage made by infusing leaves, fruits, seeds, herbs, or a combination of these.

An example of a fermented tea-based beverage is 'Kombucha'. This is a beverage that results from the fermentation of sweetened tea by acetic acid bacteria and yeast cultures. Kombucha is created by the action of a symbiosis of microorganisms, namely yeasts and bacteria, in the form of a thick gelatinous, shiny fungus mesh membrane, which forms a symbiosis of yeast cells with different bacteria. Kombucha mainly develops glucuronic acid, lactic acid, acetic acid and various vitamins in the beverage.

In a first aspect, the invention relates to a yeast strain used in the production of a fermented beverage, wherein the yeast strain is a hybrid obtained by a mass-mating hybridisation process between haploid spores selected from *Saccharomyces cerevisiae* strain Y927, strain Y115, strain WI011, strain WI017 and strain WI018, or wherein the yeast strain is an inbred strain of said hybrid.

*Saccharomyces cerevisiae* is a yeast with many interesting physiological characteristics that makes it very suitable for industrial fermentations. Firstly, this yeast is able to outperform most other yeasts in industrial fermentations of wine, beer, cider, etc. This fitness advantage can be attributed to several characteristics, including high stress tolerance (e.g. to ethanol and high temperature), fast and efficient carbon metabolism, and the ability to grow under aerobic and anaerobic conditions. Second, *S. cerevisiae* yeasts produce many desirable flavours, such as volatile esters and higher alcohols, and only a few off-flavours. Finally, these yeast cells do not produce specific toxins that would be harmful to humans, making them safe for use in food fermentations, as evidenced by the status 'Generally Recognized As Safe (GRAS)' and the 'Qualified Presumption of Safety (QPS)' of *S. cerevisiae*. '*Saccharomyces cerevisiae* strain Y927' is a yeast strain known in the literature (Meersman, et al., 2015), that can survive for a long time and has a high tolerance to high temperature. This is also called 'thermotolerance'. 'Basic thermotolerance' refers to the ability of an organism to withstand high temperatures without prior acclimation. 'Acquired thermotolerance' refers to the ability to withstand high temperatures after prior exposure to moderate temperatures. In addition, this strain produces spores efficiently and is tolerant to ethanol.

'*Saccharomyces cerevisiae* strain Y115' is also a yeast strain known in the literature (Meersman, et al., 2015) and from the bioethanol industry, with a high thermotolerance, longevity, tolerance to ethanol and efficient sporulation.

In addition, yeast strains '*Saccharomyces cerevisiae* strain WI011, strain WI017 and strain WI018' are known from the literature (Gallone, et al., 2016), as yeast strains originating from the wine industry. Like the previous *S. cerevisiae* strains Y115 and Y927, these three yeast strains are also thermotolerant and long-living.

Thermotolerant yeast strains of the present invention are capable of growing at a temperature of 42° C.

As part of the hybridisation process of the present invention, *S. cerevisiae* yeast strains Y927, Y115, WI011, WI017 and WI018 were tested or assayed to generate a set of hybrid yeast strains. This can be, for example, a mass-mating assay.

'Mass-mating' means that more than two spores are allowed to mate or hybridise with each other.

For this, the said yeast strains were sporulated, and the (haploid) spores were harvested. These were allowed to hybridise to diploid hybrids.

After this, the pool of newly formed hybrids may be subjected, for example, to a high temperature incubation (e.g., 42° C. for a particular period of time) to select for hybrids with a high temperature tolerance. Longevity and other stress factors can optionally be added here to select for hybrids with those characteristics. These stress factors and methods of subjecting yeast strains to them are known to those of skill in the art. A non-exhaustive list of possible stress factors is high temperature, as already mentioned above, low temperature, ethanol, dryness, aerobic environment, anaerobic environment, a poor nutrient source, and so on.

Genetic fingerprinting or sequencing can be used to determine whether the diploids are the result of mating cells from the same parent or from two different parental strains. This allows selection of diploids resulting from outbreeding of *S. cerevisiae* yeast strains Y927, Y115, WI011, WI017 and WI018. These are the 'hybrids' of the present invention.

These hybrids can then be re-subjected to a mass-mating assay or any other assay, as known to those of skill in the art, that allows spores of these strains to mate. In this case, by genetic fingerprinting, sequencing or another technique known to those of skill in the art, diploids resulting from inbreeding are selected. These are the 'inbred strains of the hybrid' of the present invention.

The advantage of the yeast strain of the present invention is that it has a combination of characteristics of both parental strains (hybrids) or stronger characteristics than the one parental hybrid strain (inbred strains). These characteristics include thermotolerance, longevity, efficient sporulation, ethanol tolerance, a fast and efficient carbon metabolism, the ability to grow under aerobic and anaerobic conditions, producing many desirable flavours and few off-flavours, and/or not producing toxins harmful to humans.

Like parent strains Y927, Y115, WI011, WI017 and/or WI018, this yeast strain is long-living and thermotolerant.

As previously indicated, 'long-living' or similar terms in the context of the present invention are defined as being capable of carrying out metabolic and/or enzymatic activity, at least for 100 days. An easily measurable and visual example of this is growth and/or cell division, but this metabolic and/or enzymatic activity is not limited to growth and/or cell division.

Longevity and thermotolerance offer some advantages, not least in terms of the shelf life of the resulting products. For example, the beer market is global, and a long shelf life as well as tolerance to more extreme environmental conditions is important.

In one embodiment, the yeast strain of the present invention is capable of growing at a temperature of 42° C. and for a period of at least 5 days in a nutrient rich environment.

In a further embodiment, this nutrient rich environment consists of a solid, culture medium consisting of water, yeast extract (1% w/v), bacteriological peptone (2% w/v), glucose (2% w/v) and agar (2% w/v).

In a further preferred embodiment, $10^6$ cells are inoculated on such culture medium and incubated for 5 days to observe growth.

In one embodiment, the yeast strain is capable of converting aldehydes to their corresponding alcohol. Aldehydes are known for their strong influence on the taste of beverages, such as beer, and an excess of certain aldehydes, such as methylpropanal and benzaldehyde, are often associated with bad taste. The formation or build-up of certain aldehydes can thus be avoided. Aldehydes can be converted to their corresponding alcohol.

In one embodiment, the aldehyde furfural is converted by the yeast strain through reducing properties of this strain. For example, furfural is reduced to furfuryl alcohol.

Furfural is an aldehyde that is formed in beer and is used, among other things, to predict and/or determine the age of the beverage. Furfural is therefore also called an age indicator, and can therefore be used to determine shelf life. The more furfural is present in the beverage, the more other aldehydes are present in the beverage which often cause a bad taste.

Furfural is formed in significant quantities during the 'mashing' and 'hopping' processes, part of the beer brewing process. However, almost all furfural is reduced by yeasts during the fermentation process. Furfural is again produced during storage and maturation of the beer or another alcoholic fermented beverage.

It is widely recognized that if the yeast strain is capable of converting furfural into another compound, such as by reduction to the corresponding alcohol, this yeast strain will also be able to reduce some other aldehydes, and thus dispel the related bad taste. A long lifespan of such a yeast strain is important because it can counter the build-up of furfural and other aldehydes over a longer period of time, and thus will have a positive effect on the shelf life of beverages.

Furfural content can be measured by an extraction step followed by a gas chromatography step and a mass spectrometry step. For example, this component can be measured by solid phase microextraction (SPME) followed by gas chromatography and mass spectrometry.

In more detail, for beer, beer chemicals will attach to a fibre during the solid phase microextraction. However, the fibre is first coated, for example with pentafluorobenzylhydroxylamine (PFBHA), as this facilitates the detection of aldehydes. This is necessary since aldehydes are present in very low concentrations. Gas chromatography then separates the compounds that were adsorbed to the fibre. Finally, the secreted compounds, including furfural, can be detected by mass spectrometry.

Other techniques for detecting and measuring furfural exist and will be known to those of skill in the art.

In one embodiment of the present invention, the yeast strain has a lifespan of at least 100 days in an alcohol-rich environment such as beer.

In the present context, an 'alcohol-rich environment' means an environment with an alcohol content of at least 0.2% (v/v). The alcohol in the alcohol-rich environment is preferably ethanol.

'Lifespan' in this case is defined as the time during which the strain is able to perform metabolic and/or enzymatic activity. This can be growth and/or cell division, but need not be limited to growth and/or cell division. The lifespan of the yeasts of the present invention is twice as long as the mean survival time (or thus metabolically and/or enzymatically active time) (50-60 days) of an average commercial (beer) yeast strain. If the yeast strain survives longer, it can, as previously described, reduce bad-tasting components for longer, so that the taste and quality remain good for longer, and thus the shelf life of the beverage is extended. When this yeast strain is also thermotolerant, as already described above, the yeast strain can still function at higher temperatures, such as during transport throughout the global market, and keep the quality of the beverage higher for longer.

In one embodiment of the present invention, the yeast strain as described above in one of the foregoing embodiments is a yeast strain deposited with the Belgian Coordinated Collection of Microorganisms (BCCM)—Université catholique de Louvain—Mycothèque de l'Université catholique de Louvain (MUCL), as Deposit ID No. 58105 and 58106.

In one embodiment of the present invention, the yeast strain is a mutant of a strain deposited with the Belgian Coordinated Collection of Microorganisms (BCCM)—Université catholique de Louvain-Mycothèque de l'Université catholique de Louvain (MUCL), as Deposit ID No. 58105 and 58106. Preferably, this mutant yeast strain is still capable of growing at a temperature of 42° C. and for a period of at least 5 days in a nutrient rich environment. Also preferably, this mutant yeast strain is still capable of converting aldehydes to their corresponding alcohol.

In one embodiment of the present invention, the yeast strain exhibits at least 95% sequence identity with a yeast strain as deposited with the Belgian Coordinated Collection of Microorganisms (BCCM)—Université catholique de Louvain-Mycothèque de l'Université catholique de Louvain (MUCL), as Deposit ID No. 58105 and 58106. Preferably the yeast strain has at least 95.5%, more preferably 96%, more preferably 96.5%, more preferably 97%, more preferably 97.5%, more preferably 98%, more preferably 98.1%, more preferably 98.2%, more preferably 98.3%, more preferably 98.4%, more preferably 98.5%, more preferably 98.6%, more preferably 98.7%, more preferably 98.8%, most preferably 98.9%, more preferably 99.0%, more preferably 99.1%, more preferably 99.2%, more preferably 99.3%, more preferably 99.4%, more preferably 99.5%, more preferably 99.6%, more preferably 99.7%, more preferably 99.8%, most preferably 99.9% genomic sequence identity with a yeast strain as deposited with the Belgian Coordinated Collection of Microorganisms (BCCM)—Université catholique de Louvain-Mycothèque de l'Université catholique de Louvain (MUCL), as Deposit ID No. 58105 and 58106. Preferably, this yeast strain is still capable of growing at a temperature of 42° C. and for a period of at least 5 days in a nutrient rich environment. Also preferably, this yeast strain is still capable of converting aldehydes to their corresponding alcohol.

In a second aspect, the invention relates to a yeast slurry comprising at least $10^6$ cells/ml, of a yeast strain of the present invention as described in at least one of the above embodiments. Preferably, the yeast slurry comprises at least $2*10^6$ cells/ml, more preferably at least $3*10^6$ cells/ml, more preferably at least $4*10^6$ cells/ml, more preferably at least $5*10^6$ cells/ml, more preferably at least $6*10^6$ cells/ml, more preferably at least $7*10^6$ cells/ml, more preferably at least $8*10^6$ cells/ml, more preferably at least $9*10^6$ cells/ml, with more preferably at least $10^7$ cells/ml, more preferably the yeast slurry comprises at least $2*10^7$ cells/ml, more preferably at least $3*10^7$ cells/ml, more preferably at least $4*10^7$ cells/ml, more preferably at least $5*10^7$ cells/ml, more preferably at least $6*10^7$ cells/ml, more preferably at least $7*10^7$ cells/ml, more preferably at least $8*10^7$ cells/ml, more preferably at least $9*10^7$ cells/ml, more preferably at least $10^8$ cells/ml. More preferably, the yeast slurry comprises at least $2*10^8$ cells/ml, more preferably at least $3*10^8$ cells/ml, more preferably at least $4*10^8$ cells/ml, more preferably at least $5*10^8$ cells/ml, more preferably at least $6*10^8$ cells/ml, more preferably at least $7*10^8$ cells/ml, more preferably at least $8*10^8$ cells/ml, more preferably at least $9*10^8$ cells/ml, with more preferably, at least $10^9$ cells/ml of a yeast strain of the present invention as described in at least one of the above embodiments. A person skilled in the art will understand that a higher concentration of yeast cells in a slurry is also possible. This yeast slurry can be used in a beverage fermentation process.

In one embodiment, the slurry is obtained by adding cells, in particular by inoculating the yeast strain, to a wort.

In a further embodiment, this inoculated wort is given time to grow and divide the cells. Preferably, this is done at a temperature that is ideal for the yeast strain to grow and divide.

In other words, the yeast cells will propagate in the wort. By 'propagation' is understood the cultivation of yeast to produce a large biomass of yeast of known origin in the shortest possible time, here with the main purpose of using it for fermentation. The known origin implies that the cultured yeast is of the desired specific strain. Preferably, the wort will be heated to a temperature at which the yeast strain can best propagate.

The yeast strain of the present invention can be added to a sugar-rich non-fermented beverage. This can be a wort. Wort contains enough nutrients, including sugars, for the yeast to propagate.

In one embodiment, at least $10^6$ cells of yeast will be added per ml of beverage.

In one embodiment, for the present invention, the beverage or wort will be preheated to a temperature of 24° C. The yeast strain is in this way in an ideal environment for growing until a sufficient number of yeast cells, and thus a sufficiently large density or biomass, has been reached, and thus a yeast slurry is formed.

The advantage of the yeast slurry is that it already contains a large amount of concentrated yeast cells, whereby this slurry can easily be used as a starter culture for an inoculation in a fermentation process, such as in a beverage such as beer.

In one embodiment, the yeast slurry further comprises at least one further yeast strain, different from said hybrid or inbred yeast strain.

When two or more yeast strains are inoculated together, it is referred to as co-inoculation. Thus, the yeast strain of the present invention can be co-inoculated with a typical brewer's yeast. For example, the typical brewer's yeast can give the beverage its typical characteristics such as taste, alcohol percentage, etc., while the yeast strain of the present invention can continue to convert 'staling' components, for example during transport at higher temperatures or for a longer time than the typical brewer's yeast can do so.

In a further embodiment, the yeast slurry further comprises an additional *Saccharomyces cerevisiae* strain, a Brettanomyces strain or a mixture of said yeasts.

In one embodiment, the ratio between the hybrid or inbred yeast strain of the invention and the further yeast strains is between 1:1000 and 1:10.so that the yeast strain of the invention represents 0.1-10% of the total yeast cells.

In a further aspect, the invention relates to a method for brewing a fermented beverage, wherein a yeast strain or yeast slurry of the present invention is added to a beverage.

One skilled in the art will appreciate that the yeast strain and/or yeast slurry of the present invention can be used in a method and in a beverage as described above and below. Accordingly, all aspects of the present invention are interrelated. All of the features and advantages as described in the aspect relating to the yeast strain, yeast slurry, method or beverage, as described both above and below, may relate to any of these aspects, even if described in conjunction with a specific aspect.

The yeast strain of the present invention can be added to a sugar-rich non-fermented beverage. This can be a wort. In this way, the yeast strain has sufficient nutrients, such as sugars, to grow until a sufficient number of yeast cells, and thus a sufficiently high density, has been reached. This creates a concentrated yeast slurry.

The beverage can be an alcoholic or a non-alcoholic fermented beverage.

In one embodiment of the method, the yeast strain, whether or not in the form of a yeast slurry, is added to a beverage by inoculation.

In one embodiment of the method, the yeast strain or yeast slurry is added to a density of about $10^2$ to about $10^8$ cells/ml. The yeast strain or yeast slurry is added up to a density of around $10^2$ cells/ml, or up to around $2*10^2$ cells/ml, or up to around $3*10^2$ cells/ml, or up to around $4*10^2$ cells/ml, or up to around $5*10^2$ cells/ml, or up to around $6*10^2$ cells/ml, or up to around $7*10^2$ cells/ml, or up to around $8*10^2$ cells/ml, or up to around $9*10^2$ cells/ml. The yeast strain or yeast slurry is added up to a density of around $10^3$ cells/ml, or up to around $2*10^3$ cells/ml, or up to around $3*10^3$ cells/ml, or up to around $4*10^3$ cells/ml, or up to around $5*10^3$ cells/ml, or up to around $6*10^3$ cells/ml, or up to around $7*10^3$ cells/ml, or up to around $8*10^3$ cells/ml, or up to around $9*10^3$ cells/ml. The yeast strain or yeast slurry is added up to a density of around $10^4$ cells/ml, or up to around $2*10^4$ cells/ml, or up to around $3*10^4$ cells/ml, or up to around $4*10^4$ cells/ml, or up to around $5*10^4$ cells/ml, or up to around $6*10^4$ cells/ml, or up to around $7*10^4$ cells/ml, or up to around $8*10^4$ cells/ml, or up to around $9*10^4$ cells/ml. The yeast strain or yeast slurry is added up to a density of around $10^5$ cells/ml, or up to around $2*10^5$ cells/ml, or up to around $3*10^5$ cells/ml, or up to around $4*10^5$ cells/ml, or up to around $5*10^5$ cells/ml, or up to around $6*10^5$ cells/ml, or up to around $7*10^5$ cells/ml, or up to around $8*10^5$ cells/ml, or up to around $9*10^5$ cells/ml. The yeast strain or yeast slurry is added up to a density of around $10^6$ cells/ml, or up to around $2*10^6$ cells/ml, or up to around $3*10^6$ cells/ml, or up to around $4*10^6$ cells/ml, or up to around $5*10^6$ cells/ml, or up to around $6*10^6$ cells/ml, or up to around $7*10^6$ cells/ml, or up to around $8*10^6$ cells/ml, or up to around $9*10^6$ cells/ml. The yeast strain or yeast slurry is added up to a density of around $10^7$ cells/ml, or up to around $2*10^7$ cells/ml, or up to around $3*10^7$ cells/ml, or up to around $4*10^7$ cells/ml, or up to around $5*10^7$ cells/ml, or up to around $6*10^7$ cells/ml, or up to around $7*10^7$ cells/ml, or up to around $8*10^7$ cells/ml, or up to around $9*10^7$ cells/ml or up to around $10^8$ cells/ml.

In one embodiment of the method, at least one further yeast strain, different from said hybrid or inbred yeast strain of the present invention, is inoculated into the beverage.

Thus, the yeast strain of the present invention can be co-inoculated with a typical brewer's yeast, as described above.

In a further embodiment, this additional yeast strain is a *Saccharomyces cerevisiae* strain, a Brettanomyces strain or a mixture of said yeasts.

In one embodiment, the ratio between the hybrid or inbred yeast strain of the invention and the further yeast strains is between 1:1000 and 1:10.so that the yeast strain of the invention represents 0.1-10% of the total yeast cells.

In one embodiment of the method, the yeast strain or yeast slurry can be used for the fermentation of the beverage.

In this case, the yeast strain or yeast slurry of the present invention can be added to a beverage to be fermented by inoculation to a density of preferably around $10^5$ to around $10^8$ cells/ml.

Preferably, the yeast strain or yeast slurry is added up to a density of around $10^5$ cells/ml, or up to around $2*10^5$ cells/ml, or up to around $3*10^5$ cells/ml, or up to around $4*10^5$ cells/ml, or up to around $5*10^5$ cells/ml, or up to around $6*10^5$ cells/ml, or up to around $7*10^5$ cells/ml, or up to around $8*10^5$ cells/ml, or up to around $9*10^5$ cells/ml. The yeast strain or yeast slurry is added up to a density of around $10^6$ cells/ml, or up to around $2*10^6$ cells/ml, or up to around $3*10^6$ cells/ml, or up to around $4*10^6$ cells/ml, or up to around $5*10^6$ cells/ml, or up to around $6*10^6$ cells/ml, or up to around $7*10^6$ cells/ml, or up to around $8*10^6$ cells/ml, or up to around $9*10^6$ cells/ml. The yeast strain or yeast slurry is added up to a density of around $10^7$ cells/ml, or up to around $2*10^7$ cells/ml, or up to around $3*10^7$ cells/ml, or up to around $4*10^7$ cells/ml, or up to around $5*10^7$ cells/ml, or up to around $6*10^7$ cells/ml, or up to around $7*10^7$ cells/ml, or up to around $8*10^7$ cells/ml, or up to around $9*10^7$ cells/ml or up to around $10^8$ cells/ml.

In one embodiment of the method, the yeast strain or yeast slurry can be used for refermentation of the beverage. Preferably, the yeast strain or yeast slurry is then added up to a density of around $10^2$ to $10^7$ cells/ml.

Preferably, the yeast strain or yeast slurry is added up to a density of around $10^2$ cells/ml, or up to around $2*10^2$ cells/ml, or up to around $3*10^2$ cells/ml, or up to around $4*10^2$ cells/ml, or up to around $5*10^2$ cells/ml, or up to around $6*10^2$ cells/ml, or up to around $7*10^2$ cells/ml, or up to around $8*10^2$ cells/ml, or up to around $9*10^2$ cells/ml. The yeast strain or yeast slurry is added up to a density of around $10^3$ cells/ml, or up to around $2*10^3$ cells/ml, or up to around $3*10^3$ cells/ml, or up to around $4*10^3$ cells/ml, or up to around $5*10^3$ cells/ml, or up to around $6*10^3$ cells/ml, or up to around $7*10^3$ cells/ml, or up to around $8*10^3$ cells/ml, or up to around $9*10^3$ cells/ml. The yeast strain or yeast slurry is added up to a density of around $10^4$ cells/ml, or up to around $2*10^4$ cells/ml, or up to around $3*10^4$ cells/ml, or up to around $4*10^4$ cells/ml, or up to around $5*10^4$ cells/ml, or up to around $6*10^4$ cells/ml, or up to around $7*10^4$ cells/ml, or up to around $8*10^4$ cells/ml, or up to around $9*10^4$ cells/ml. The yeast strain or yeast slurry is added up to a density of around $10^5$ cells/ml, or up to around $2*10^5$ cells/ml, or up to around $3*10^5$ cells/ml, or up to around $4*10^5$ cells/ml, or up to around $5*10^5$ cells/ml, or up to around $6*10^5$ cells/ml, or up to around $7*10^5$ cells/ml, or up to around $8*10^5$ cells/ml, or up to around $9*10^5$ cells/ml. The yeast strain or yeast slurry is added up to a density of around $10^6$ cells/ml, or up to around $2*10^6$ cells/ml, or up to around $3*10^6$ cells/ml, or up to around $4*10^6$ cells/ml, or up to around $5*10^6$ cells/ml, or up to around $6*10^6$ cells/ml, or up to around $7*10^6$ cells/ml, or up to around $8*10^6$ cells/ml, or up to around $9*10^6$ cells/ml, or up to around $10^7$ cells/ml.

As mentioned earlier, 'refermentation' means that a second or third fermentation of the wort continues in a, usually new fermenter, after a first or primary fermentation step. During this second fermentation, much of the remaining yeast will settle at the bottom of the fermentation vessel, resulting in a less cloudy product. This also gives the opportunity to allow the fermenting beverage to mature. Refermentation by adding *Saccharomyces* or another yeast will give the beer its specific taste and colour. The reducing character of the yeast will also prevent oxidation processes.

Refermentation is initiated by the addition of a viable yeast (population). When there is no more fermentable residual sugar, sugar or wort or both can be added in a process known as priming.

Preferably, in the present invention, sugar is added for priming to a density of around 0.05° P to around 5.0° P. Preferably it is from around 0.07-5.0° P, more preferably 0.09-5.0° P, more preferably 0.11-5.0° P, more preferably 0.13-5.0° P, more preferably 0.15-5.0° P, more preferably 0.17-5.0° P, more preferably 0.19-5.0° P, more preferably 0.20-5.0° P. More preferably 0.05-4.5° P, more preferably 0.07-4.5° P, more preferably 0.09-4.5° P, more preferably 0.11-4.5° P, more preferably 0.13-4.5° P, more preferably 0.15-4.5° P, more preferably 0.17-4.5° P, more preferably 0.19-4.5° P, more preferably 0.20-4.5°P. More preferably it is from around 0.05-4.0° P, more preferably 0.07-4.0° P, more preferably 0.09-4.0° P, more preferably 0.11-4.0° P, more preferably 0.13-4.0° P, more preferably 0.15-4.0° P, more preferably 0.17-4.0° P, more preferably 0.19-4.0° P, more preferably 0.20-4.0° P. More preferably 0.05-3.5° P, more preferably 0.07-3.5° P, more preferably 0.09-3.5° P, more preferably 0.11-3.5° P, more preferably 0.13-3.5° P, more preferably 0.15-3.5° P, more preferably 0.17-3.5° P, more preferably 0.19-3, 5° P, more preferably 0.20-3.5° P. More preferably it is from around 0.05-3.0° P, more preferably 0.07-3.0° P, more preferably 0.09-3.0° P, more preferably 0.11-3.0° P, more preferably 0.13-3.0° P, more preferably 0.15-3.0° P, more preferably 0.17-3.0° P, more preferably 0.19-3.0° P, more preferably 0.20-3.0° P. More preferably 0.05-2.5° P, more preferably 0.07-2.5° P, more preferably 0.09-2.5° P, more preferably 0.11-2.5° P, more preferably 0.13-2.5° P, more preferably 0.15-2.5° P, more preferably 0.17-2.5° P, more preferably 0.19-2.5° P, more preferably 0.20-2.5° P. More preferably it is from 0.05-2.0° P, more preferably 0.07-2.0° P, more preferably 0.09-2.0° P, more preferably 0.11-2.0° P, more preferably 0.13-2.0° P, more preferably 0.15-2.0° P, more preferably 0.17-2.0° P, more preferably 0.19-2.0° P, more preferably 0.20-2.0° P. More preferably, sugar is added to a density of 0.05-1.75° P. More preferably 0.07-1.75° P, more preferably 0.09-1.75° P, more preferably 0.11-1.75° P, more preferably 0.13-1.75° P, more preferably 0.15-1.75° P, more preferably 0.17-1.75° P, more preferably 0.19-1.75° P, more preferably 0.20-1.75° P. More preferably 0.005-1.5° P, more preferably 0.07-1.5° P, more preferably 0.09-1.5° P, more preferably 0.11-1.5° P, more preferably 0.13-1.5°P, more preferably 0.15-1.5° P, more preferably 0.17-1.5° P, more preferably 0.19-1.5° P, more preferably 0.20-1.5° P. More preferably it is from around 0.05-1.25° P, more preferably 0.07-1.25° P, more preferably 0.09-1.25° P, more preferably 0.11-1.25° P, more preferably 0.13-1.25° P, more preferably 0.15-1.25° P, more preferably 0.17-1.25° P, more preferably 0.19-1.25° P, more preferably 0.20-1.25° P. More preferably it is from around 0.07-1.0° P, more preferably 0.09-1.0° P, more preferably 0.11-1.0° P, more preferably 0.13-1.0° P, more preferably 0.15-1.0° P, more preferably 0.17-1.0° P, more preferably 0.19-1.0° P, more preferably 0.20-1.0° P. More preferably, sugar is added to a density of 0.05-0.75° P. More preferably 0.07-0.75° P, more preferably 0.09-0.75° P, more preferably 0.11-0.75° P, more preferably 0.13-0.75° P, more preferably 0.15-0.75° P, more preferably 0.17-0.75° P, more preferably 0.19-0.75° P, more preferably 0.20-0.75° P. More preferably 0.05-0.5° P, more preferably 0.07-0.5° P, more preferably 0.09-0.5° P, more preferably 0.11-0.5° P, more preferably 0.13-0.5° P, more preferably 0.15-0.5° P, more preferably 0.17-0.5° P, more preferably 0.19-0.5° P, more preferably 0.20-0.5° P. More preferably 0.05-0.25° P, more preferably 0.07-0.25° P, more preferably 0.09-0.25° P, more preferably 0.11-0.25° P, more preferably 0.13-0.25° P, more preferably 0.15-0.25° P, more preferably 0.17-0.25° P, more preferably 0.19-0.25° P, more preferably 0.20-0.25° P. More preferably 0.05-0.22° P, more preferably 0.07-0.22° P, more preferably 0.09-0.22°P, more preferably 0.11-0.22° P, more preferably 0.13-0.22° P, more preferably 0.15-0.22° P, more preferably 0.17-0.22° P, more preferably 0.19-0.22°P, more preferably 0.20-0.22° P, most preferably 0.19-0.21° P.

This is an ideal amount of sugar, as a nutrient source for the yeast strain, for the refermentation of a beverage using the yeast strain of the present invention.

In a preferred embodiment, the fermentation continues in a bottle, in a keg or in a container.

Refermentation in a bottle can be referred to as 'bottle fermentation', 'bottle refermentation', 'bottle conditioning' or 'bottle kräusening'. Some fermented beverages undergo additional fermentation in the bottle instead of a new fermenter. This can be a second and/or third fermentation. Due to secondary fermentation in the bottle, the beverage will be saturated with $CO_2$. The foam production is promoted, and the alcohol content will also increase slightly. The bottle-conditioned beverages can be bottled unfiltered directly from the fermentation or conditioning tank or filtered and then resealed with yeast.

The bottling of beer is preferably done under vacuum, so that no oxidation can occur. The filled and sealed bottles are then usually placed in a warm room for a few days, at a temperature at which the yeast can optimally referment in the bottle, such as at a temperature of 20-25° C.

When this refermentation continues in a keg, it is referred to as 'keg conditioning', 'keg fermentation' or keg refermentation'. In addition, refermentation can also continue in a container. Then we speak of 'container conditioning', 'container fermentation' or 'container refermentation'.

In a final aspect, the present invention relates to a malt or tea-based beverage obtained from a fermentation process, wherein the beverage comprises a yeast strain according to the present invention.

In a preferred embodiment, this alcoholic beverage is obtained by a method of the present invention.

One of skill in the art will appreciate that the yeast strain and/or yeast slurry of the present invention can be used in a method and in a described beverage, and for the production of the malt or tea-based beverage of the present invention. Accordingly, all aspects of the present invention are interrelated. All of the features and advantages as described in the aspect relating to the yeast strain, yeast slurry, method or beverage, as described both above and below, may relate to any of these aspects, even if described in conjunction with a specific aspect.

A beverage comprising a yeast strain of the present invention can be distinguished from a beverage for which this yeast strain was not used during production. The yeast strain has a unique genetic fingerprint or unique genetic profile. In addition, DNA sequencing can also be used to identify the yeast strain in the beverage.

In one embodiment of the malt or tea-based beverage, the yeast strain of the present invention is responsible for the fermentation of the beverage.

In another or further embodiment of the malt or tea-based beverage, the yeast strain is responsible for the fermentation of the beverage. This refermentation can continue in the bottle, in a keg or in a container, as already described above.

The malt or tea-based beverage of the present invention can be alcoholic or non-alcoholic.

The beverage of the present invention can be kombucha. 'Kombucha', is a beverage that results from the fermentation of sweetened tea by acetic acid bacteria and yeast cultures. Kombucha is created by the action of a symbiosis of microorganisms, namely yeasts and bacteria, in the form of a thick gelatinous, shiny fungus mesh membrane, which forms a symbiosis of yeast cells with different bacteria. Kombucha mainly develops glucuronic acid, lactic acid, acetic acid and various vitamins in the beverage.

The beverage of the present invention can be a beer.

In a preferred embodiment, the beverage of the present invention is beer. The yeast strain is preferably responsible for the fermentation of the beverage or of the beer.

In a preferred embodiment, the alcoholic beverage has an alcohol percentage of 7.5-10.5%, an original gravity of 13.0-18.0° P, a light blond colour and EBC value of less than 9, and a bitterness of 25-45 EBU.

In one embodiment, the alcohol percentage in the alcoholic beverage is around 7.5-10.5%, preferably around 8-10.5%, more preferably around 8.5-10.5%. More preferably, the alcohol percentage is around 7.5-10.0%, more preferably around 8-10.0%, more preferably around 8.5-10.0%. More preferably, the alcohol percentage is around 7.5-9.5%, more preferably around 8-9.5%, more preferably around 8.5-9.5%.

In one embodiment, the beverage of the present invention has an original gravity of 13.0-18.0° P.

The 'original gravity' is an indication of the proportion of solids in the wort before fermentation into beer. It is a measure of the density of the solution, and thus says something about how heavy a beer is, which is why one speaks about the density of the beer. The original gravity serves as the basis for calculating the beer excise duty. Most of the solids in the wort mixture are sugars. To the extent that these sugars are fermented into alcohol, the original wort content is therefore also an indication of the later alcohol percentage. However, this is not entirely true because, depending on the yeast and the circumstances (temperature, air pressure, amount of alcohol already formed, etc.), the degree of fermentation can vary. The original gravity is currently expressed as standard in the European Union in degrees Plato, measured at 20° C. The Plato scale is an improvement of the Balling scale, which is traditionally used in the Czech Republic. The scale is specifically designed for the brewing industry and measures the ratio of fermentable sugars in the wort solution.

In one embodiment, the beverage of the present invention has an original gravity of 13.0-18.0° P. More preferably it is 13.5-18.0° P, more preferably 14.0-18.0° P, more preferably 14.5-18.0° P, more preferably 15.0-18.0° P. More preferably it is 13.5-17.5° P, more preferably 14.0-17.5° P, more preferably 14.5-17.5° P, more preferably 15.0-17.5° P. More preferably it is 13.5-17.0° P, more preferably 14.0-17.0° P, more preferably 14.5-17.0° P, more preferably 15.0-17.0° P. More preferably it is 13.5-16.5° P, more preferably 14.0-16.5° P, more preferably 14.5-16.5° P, more preferably 15.0-16.5° P. More preferably it is 13.5-16.0° P, more preferably 14.0-16.0° P, more preferably 14.5-16.0° P, and most preferably 15.0-16.0° P.

The quality of beer can be expressed in many different parameters. In addition to the taste and taste evolution over time, the visual property such as colour is also an important property for the consumer.

A 'light blonde colour' refers to an inside colour with an EBC value less than 9.

The colour of a beer can be expressed in EBC values. The determination of the EBC value is done by measuring the attenuation of light with a certain wavelength (430 nm) after passage through 1 cm beer. Here, the attenuation is a measure of the absorption of the light by the beer and the attenuation is measured as the log of the ratio of the intensity of the incoming beam over the intensity of the outgoing beam. This ratio is multiplied by a factor to obtain the EBC value. An EBC value represents a single point in the absorption spectrum of the beer. A precondition for performing an EBC measurement is that the beer sample is free from turbidity. Another method for determining the EBC value of beer is comparison of the beer colour with a standardised disc comparator. An important reaction that has a major influence on the colouration of the wort is the Maillard reaction. In fact, this is a series of reactions that occur during the heating of mixtures comprising proteins, peptides, amino acids and reducing sugars with an aldehyde or ketone function. The Maillard reaction results in a non-enzymatic brown colouring and a complexity of organic compounds. These organic compounds are responsible for taste and odour impressions in the beer.

In one embodiment, the beverage of the present invention has a colour with an EBC value of less than 9.0, preferably the EBC value is less than 8.5, preferably the EBC value is less than 8.0, preferably the EBC is value less than 7.5, preferably the EBC value is less than 7.0, preferably the EBC value is less than 6.5, preferably the EBC value is less than 6.0, preferably the EBC value is less than 5.5, preferably less than 5.0.

In addition, the 'bitterness' is also an important characteristic of beer. The bitterness is expressed in EBU (European Bitterness Unit). 1 EBU is equated with 1 mg iso-alpha acid per litre of beer. Beers with an EBU value between 5 and 15 are categorised under slightly bitter beers. Strongly bitter beers have an EBU value of or more. The beer type is of course also important: a lager with a bitterness of EBU is already experienced by many as very bitter.

The beverage of the present invention, in one embodiment, has a bitterness of 25-EBU. Preferably the bitterness is between 30-45 EBU, preferably between 35-45 EBU, preferably between 40-45 EBU. Preferably the bitterness is between 25-40 EBU, preferably between 30-40 EBU, preferably between 35-40 EBU. Preferably the bitterness is between 25-35 EBU, preferably between 30-35 EBU.

In what follows, the invention is described by way of non-limiting examples illustrating the invention, and which are not intended to and should not be interpreted as limiting the scope of the invention.

EXAMPLES

Example 1

It has already been shown that yeasts can provide protection against beer aging and staling. The precise mechanisms are not fully known, but it is believed that the reducing metabolism of live yeast cells, among other things, removes residual oxygen in the bottle, preventing oxidative degradation reactions, and converts staling aldehydes into their corresponding (less bad tasting) alcohols. An example of this is the conversion of furfural to furfuryl alcohol. Furfural is used as an age indicator in beer. The more furfural in beer, the more other aldehydes that cause a bad taste are also present. Reduction of furfural to furfuryl alcohol, and of other aldehydes to their corresponding alcohol, by yeast extends the shelf life of the beer by improving the taste and quality.

However, refermentation yeasts are not selected for long-term survival in the beer and therefore cannot prevent long-term aging of the beer. In addition, dead or 'lysed' yeast cells themselves can also have a negative influence on the taste of the beer.

To investigate whether long-living yeasts could improve the flavour stability of refermentation beer, yeasts were selected and generated that could survive in beer for a longer period of time while subjecting the beer to a high temperature profile. High temperature, as seen during transport in an increasingly globalised market, normally accelerates aging, which negatively affects the taste and thus quality of the beer.

It is important to note that 'alive' in this context means that the yeasts can still perform metabolic and/or enzymatic activity.

A hybrid yeast strain was generated which was obtained by a hybridisation process between haploid spores of *Saccharomyces cerevisiae* strain Y927 and *Saccharomyces cerevisiae* strain Y115. In addition, an inbred strain was also generated which was obtained by inbreeding of this hybrid.

*Saccharomyces cerevisiae* strain Y927 is a yeast strain known in the literature (Meersman et al., 2015), which can survive for a long time and is thermotolerant. In addition, this strain produces spores efficiently and is tolerant to ethanol. *Saccharomyces cerevisiae* strain Y115 is a yeast strain known in the literature (Meersman, et al., 2015) and from the bioethanol industry, that can survive for a long time, with a high thermotolerance, tolerance to ethanol and an efficient sporulation.

The hybrid and inbred strain of this hybrid are used for beer refermentation, also called secondary fermentation.

For this, the strain of the present invention, more specifically Deposit ID No.: 58106, is first grown in a sugar-rich wort (non-fermented beer) to obtain enough cells. Subsequently, this concentrated yeast slurry is inoculated into beer to a density of $2*10^6$ cells/ml. Sugar is then added to a density of 0.2° P (i.e. 0.2 g per 100 g of beer) and serves as a nutrient source for the yeast for refermentation in the bottle, in the keg or in a container.

As a control, a strain of a commercial brewer's yeast, more specifically LalBrew® Nottingham, is used, which is used commercially in the beer brewing process.

Survival of both strains is assessed at 10, 43, 52, 64, 81, 93 and 114 days. The results of the hybrid strain are shown in FIG. 1. While at 52 days still about $10^5$ live cells per ml (or CFU-colony forming units) are found in the control beer (b), after 64 days no detectable live cells are present in the beer. The beer with a yeast strain of the present invention (Deposit ID No.: 58106) (a) after 81 days still comprises $10^5$ live cells per ml, after 93 days still $10^4$ and after 114 still more than $10^3$ live cells per ml of beer. (c) indicates the limit of detection.

This shows that the yeast strain of the present invention survives much longer in the beer than the control yeast strain currently used in a commercial beer.

The control beer with a commercial yeast strain and the beer with the yeast strain of the present invention were also used to monitor furfural conversion by the yeast strains. Both beers undergo refermentation by addition of these yeast strains. In addition, a blank beer was added as a control, in which no yeast strain was added to the beer and thus no refermentation was started.

Figure 2A:
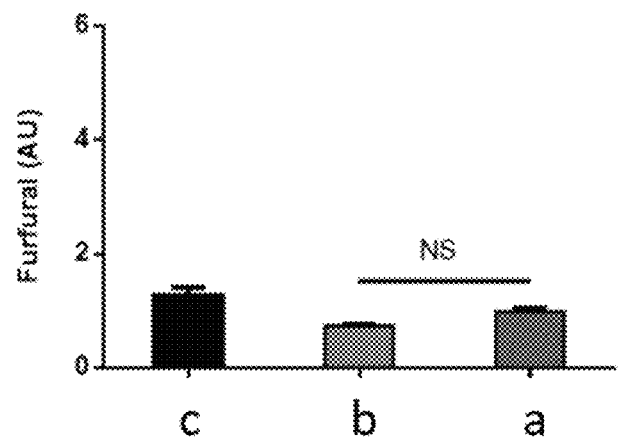
FIG. 2 schematically shows the amount of furfural in three different beer formulations after 0 (FIG. 2*a*), 81 (FIG. 2*b*) or 114 (FIG. 2*c*) days.
Figure 2B:
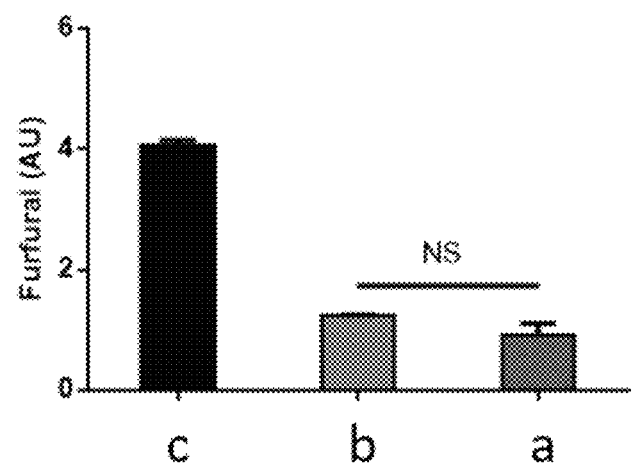
Figure 2C:
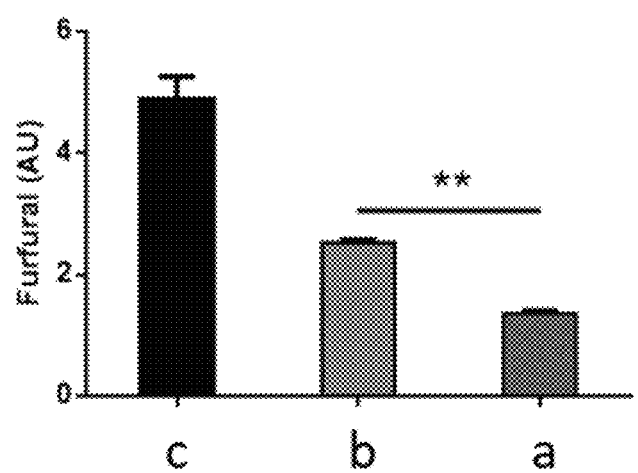

The results of furfural build-up are shown in FIG. 2. The figure shows the amount of furfural in the three different beer formulations (blank-without yeast strain (c), commercial strain LalBrew® Nottingham (b) and strain of the present invention (Deposit ID No.: 58106) (a)) at three different times of aging (day 0-FIG. 2a, day 81-FIG. 2b and day 114-FIG. 2c).

Before the onset of aging (day 0), the amount of furfural is very similar for all three beers.

After 81 days, the amount of furfural in the blank beer has increased significantly, while the refermentation beers show furfural amounts that do not differ significantly (NS) from each other. This indicates that the refermentation beers are more flavour-stable than the non-refermentation beers.

After 114 days, the furfural amount of the blank beer is still the highest, but the beer that has been re-fermented with the commercial yeast (which dies on average around day 50) now also has a furfural amount that is significant and significantly (**: $p<0.01$) higher than the beer that has been fermented with the yeast strain of the present invention (which is still alive). This indicates that an increased survival of the yeast strain improves the flavour stability of the beer.

Example 2

A beer obtained by a primary fermentation process is refermented by means of a hybrid yeast strain obtained by a hybridisation process between haploid spores of *Saccharomyces cerevisiae* strain Y927 and *Saccharomyces cerevisiae* strain Y115. For this, this yeast strain is first grown in a sugar-rich wort to obtain a concentrated yeast slurry. This yeast slurry is then inoculated into the beer to a density of $2*10^6$ cells/ml. Sugar is then also added to the beer to a density of 0.2° P (0.2 g sugar per 100 g beer) as a nutrient source for the yeast cells. The refermentation continues in beer bottles.

Example 3

Beer as obtained in Example 2 has the following properties: an alcohol percentage of 8.5%, an original gravity of 15.5° P, a light blond colour with value EBC 5.7 and a bitterness of 32 EBU.

Example 4

Beer as obtained in Example 2 has the following properties: an alcohol percentage of 9.5%, an original gravity of 15.5° P or more, a light blond colour and a bitterness of 40 EBU.

Example 5

Figure 3:
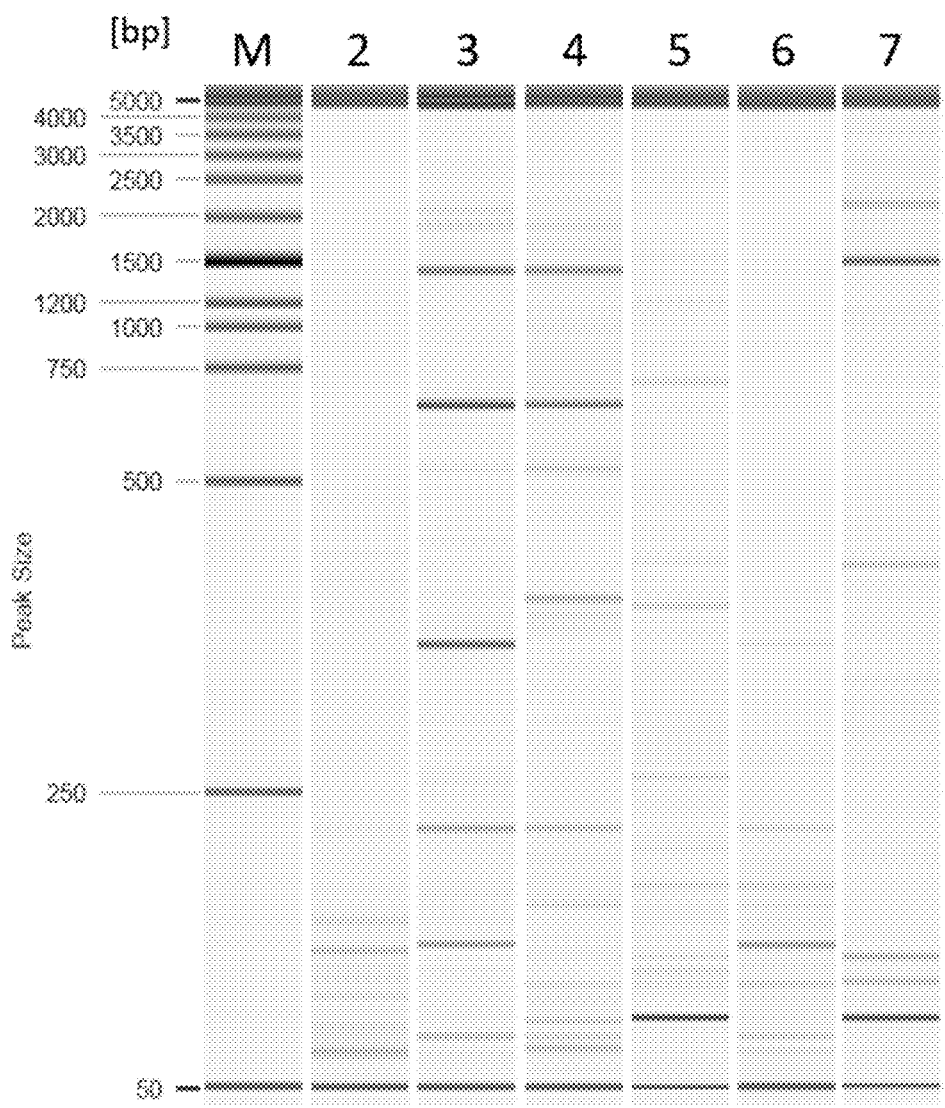
FIG. 3 schematically depicts unique genetic fingerprints from different yeast strains.

A beer comprising a yeast strain as discussed in Example 2 or another beverage comprising this yeast strain can be distinguished from a beverage for which this yeast strain was not used during production. The yeast strain has a unique genetic fingerprint or profile, as shown in FIG. 3.

The figure is an image of PCR fragments separated by gel electrophoresis. A marker (ladder-M) was loaded in the first lane. The sizes of the different PCR (polymerase chain reaction) fragments or the fragments of the marker are shown to the left of the gel in base pairs (bp). The six lanes next to the marker represent the PCR fragments of the 'interdelta' DNA from six yeast strains. This is the DNA that resides between the different transposons scattered across the yeast genome.

For example, the second lane displays the genetic fingerprint of a yeast strain (LalBrew® Nottingham) used commercially in the beer brewing process. Lanes three, four and five show the profile of three different hybrid yeast strains as discussed in Example 2, namely Deposit ID No.: 58105, Hybrid_2, and Deposit ID No.: 58106, respectively. Lanes six and seven depict the fingerprints of the parental yeast strains, *Saccharomyces cerevisiae* strain Y115 and *Saccharomyces cerevisiae* strain Y927, respectively.

As shown in this example, it is possible to distinguish yeast strains in a beverage based on their genetic fingerprint. Alternatively, DNA sequencing can also be used to identify the yeast strain in a beverage, whereby the nucleic acid sequence (the sequence of nucleotides, the building blocks of the DNA) is determined for the entire genome or part of the genome.

Example 6

The purpose of this experiment is to investigate the longevity of yeast strains according to the present invention in a beer.

A beer is inoculated with a reference brewer's yeast strain (benchmark, LalBrew® Nottingham) and optionally co-inoculated with a yeast strain of the present invention for refermentation on Day 0. The beer is then stored at 24° C. until Day 12, at 7° C. from Day 13 to Day 49, and at approximately 20° C. from Day 50 to Day 237, the end of the experiment.

Three different setups are tested, namely:
- Reference/benchmark: an inoculation with only a reference strain LalBrew® Nottingham ($10^6$ yeast cells/ml of beer),
- low co-inoculation: four co-inoculations with a reference strain LalBrew® Nottingham ($10^6$ yeast cells/ml beer) and one of four yeast strains (Hybrid_1, Hybrid_2, Hybrid_3 or Hybrid_4) according to the present invention ($5*10^5$ yeast cells/ml beer), and
- high co-inoculation: four co-inoculations with a reference strain LalBrew® Nottingham ($10^6$ yeast cells/ml beer) and one of four yeast strains (Hybrid_1, Hybrid_2, Hybrid_3 or Hybrid_4) according to the present invention ($10^6$ yeast cells/ml beer).

Hybrid_1 and Hybrid_3 are respectively the deposited yeast strains with Deposit ID No.: 58106 and 58105.

Figure 4:
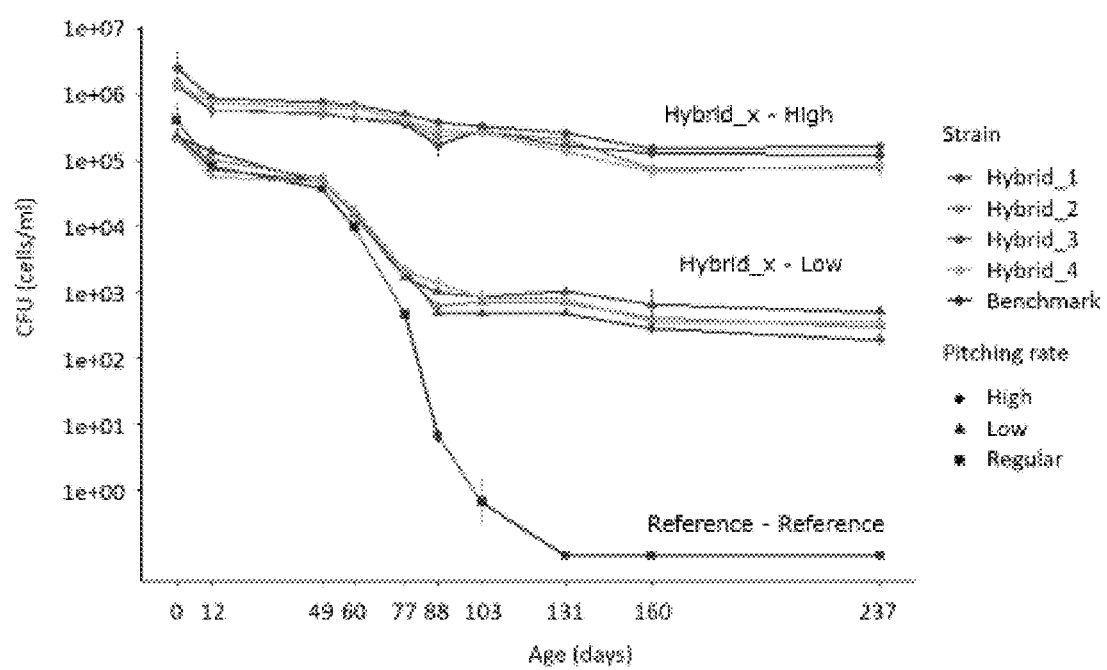
FIG. 4 schematically shows the number of live yeast cells/ml in beer plotted against time for four yeast strains according to the present invention and a reference/benchmark yeast strain in different setups.

Results are shown in FIG. 4. From this it is clear that the reference strain dies after about three months, while the yeast strains according to the present invention are still alive after about eight months, even in the case of a low co-inoculation.

The yeast strains of the present invention are longer-living in beer than a reference brewer's yeast strain under the above conditions.

Example 7

The aim of this experiment was to investigate a possible staling in the taste of 6-month-old beers which underwent a refermentation with a yeast strain according to the present invention, compared to the same beers which underwent a refermentation with a reference beer strain.

A test panel of 20 persons compared the taste of 6 month old beer fermented with a yeast strain according to the present invention (Hybrid_1 or Hybrid_3) and the same beer fermented with a reference strain/benchmark. Hybrid_1 and Hybrid_3 are respectively the deposited yeast strains with Deposit ID No.: 58106 and 58105, and the reference strain is LalBrew® Nottingham.

Figure 5:
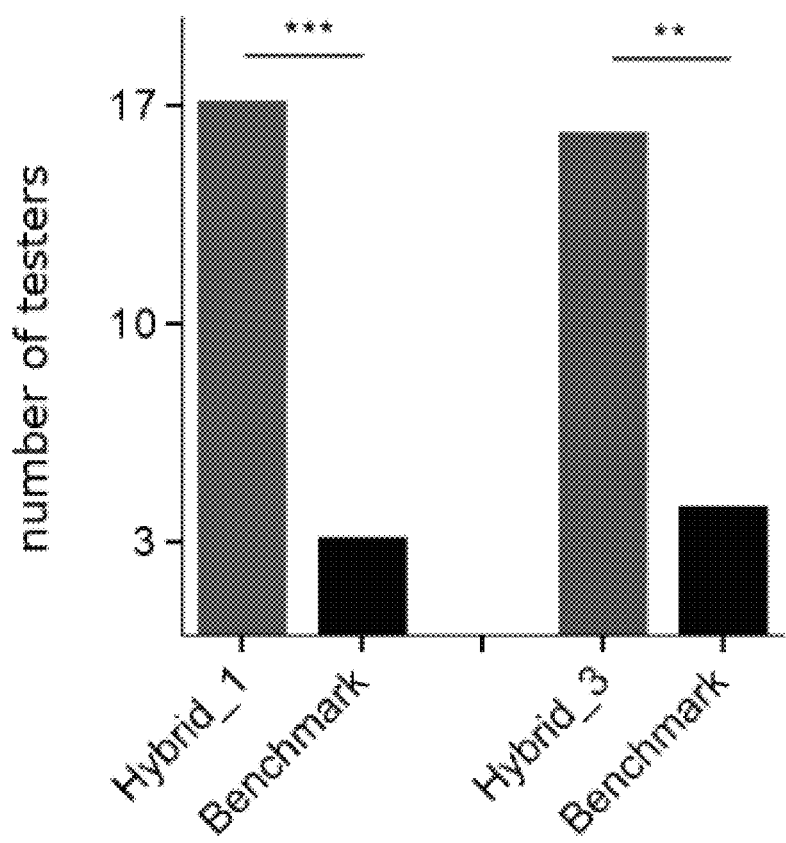
FIG. 5 shows the results of a taste test plotted against the freshness of the taste of 6-month-old beer that was either re-fermented with a yeast strain according to the present invention or with a reference/benchmark yeast strain.

Taste test results were analysed by a Bradley-Terry pairwise test and are shown in FIG. 5 (: p-value <0.01, *: p-value <0.001). The vast majority of testers (17/20 for Hybrid_1 and 16/20 for Hybrid_3) were of the opinion that the beer re-fermented with a yeast strain according to the present invention had a fresher taste than the same beer re-fermented with a reference strain/benchmark.

This shows that refermentation of beer with yeast strains according to the present invention can mitigate or reduce the staling and taste spoilage of beer.

Example 8

The aim of this experiment was to compare the taste of beers which, unlike Example 7, were not yet old, and which underwent a refermentation with a yeast strain according to the present invention, compared to the same beers which underwent a refermentation with a reference beer strain.

A triangle test was set up in which a test panel of 33 persons had to taste the fresh beer refermented with a yeast strain according to the present invention (Hybrid_1 or Hybrid_3) or the fresh beer refermented with a reference brewer's yeast strain/benchmark, and point out the product that differed from the other products. Hybrid_1 and Hybrid_3 are respectively the deposited yeast strains with Deposit ID No.: 58106 and 58105, and the reference strain is LalBrew® Nottingham.

As a control, an aged beer was compared with a fresh beer. When more than 16 of the 33 test persons identified the correct beer that differed from the other two, it was assumed that a difference in taste was indeed present.

Figure 6:
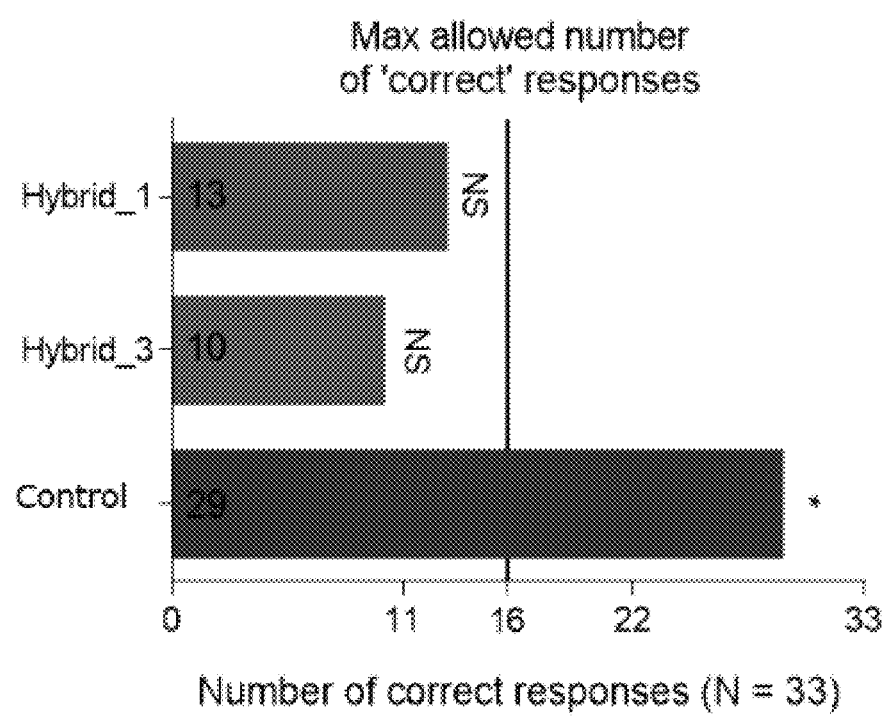
FIG. 6 shows the results of a comparative taste test of fresh beer that was either re-fermented with a yeast strain according to the present invention or with a reference/benchmark yeast strain, and a control with an aged beer.

Results are shown in FIG. 6 (NS: not significant, *: significant, triangle test compared to reference/benchmark, alpha=0.1, beta=0.05, Pd=0.4). This shows that there is no significant difference in taste between fresh beers fermented with the yeast strains of the present invention compared to fresh beers fermented with a reference yeast strain. However, the aged control beer was clearly recognised.

The combination of the experiments from Examples 7 and 8 indicates that fresh beers refermented with the yeast strains of the present invention have a similar taste to fresh beers refermented with a reference yeast strain, whereas in old beers refermented with the yeast strains of the present invention less staling or taste spoilage occurs than for old beers refermented with a reference yeast strain.

The present invention should not be construed as being limited to the embodiments described above and certain modifications or changes may be added to the examples described without having to re-evaluate the appended claims.

The invention claimed is:

1. A method for brewing a fermented beverage, wherein a yeast strain is added to a beverage and wherein the yeast strain is a hybrid obtained by a mass-mating hybridisation process between haploid spores selected from *Saccharomyces cerevisiae* strain Y927, strain Y115, strain WI011, strain WI017 and strain WI018, or wherein the yeast strain is an inbred strain of said hybrid;

wherein said yeast strain is thermotolerant in that it is capable of growing at a temperature of 42° C. for a period of at least 5 days in a nutrient-rich environment, characterized in that the yeast strain is capable of converting aldehydes into their corresponding alcohol.

2. The method of claim 1, wherein the fermented beverage is an alcoholic beverage.

3. The method according to claim 1 or 2, wherein the yeast strain is added to a beverage by means of inoculation.

4. The method of claim 3, wherein a yeast strain is inoculated into the beverage to a density of $10^2$-$10^8$ cells/ml.

5. The method according to claim 1, wherein the yeast strain is used for fermentation of the beverage.

6. The method according to claim 1, wherein the yeast strain is used for refermentation of the beverage.

7. The method according to claim 6, wherein sugar is added to an original gravity of 0.05-5.0° P as a nutrient source for the yeast strain.

8. The method according to claim 6, wherein the refermentation continues in a bottle, in a keg or in a container.

9. The method of claim 1, wherein the yeast strain is a hybrid obtained by a mass-mating hybridisation process between haploid spores selected from *Saccharomyces cerevisiae* strain Y927, strain Y115, strain WI011, strain WI017 and strain WI018, or wherein the yeast strain is an inbred strain of said hybrid;

wherein said yeast strain is thermotolerant in that it is capable of growing at a temperature of 42° C. for a period of at least 5 days in a nutrient-rich environment, characterized in that the yeast strain is capable of converting aldehydes into their corresponding alcohol.

10. The method of claim 9, wherein the yeast strain is capable of converting furfural into furfuryl alcohol.

11. The method of claim 9, wherein the yeast strain has a lifespan of at least 100 days in an alcohol-rich environment such as beer.

12. The method of claim 9, wherein:
a. a reference of said strain has been deposited with the Belgian Coordinated Collection of Microorganisms (BCCM)—Université catholique de Louvain—Mycothèque de l'Université catholique de Louvain (MUCL), as Deposit ID No.: 58105 or 58106, respectively, or wherein
b. said strain is a mutant of a yeast strain deposited as Deposit ID No.: 58105 or 58106, where the mutant yeast strain is still able to grow at a temperature of 42° C. and for a period of at least 5 days in a nutrient rich environment, and where the mutant yeast strain is still able to convert aldehydes convert to their corresponding alcohol, or where
c. said yeast strain shows at least 98% genomic sequence identity with a strain deposited as Deposit ID No.: 58105 or 58106, where the yeast strain is still able to grow at a temperature of 42° C. and for a period of at least 5 days in a nutrient rich environment, and where the yeast strain is still able to convert aldehydes to their corresponding alcohol.

* * * * *